US008648223B2

(12) United States Patent
Yoshida et al.

(10) Patent No.: US 8,648,223 B2
(45) Date of Patent: Feb. 11, 2014

(54) METHOD OF PRODUCING IODIZING AGENT, AND METHOD OF PRODUCING AROMATIC IODINE COMPOUND

(71) Applicants: Japan Science and Technology Agency, Saitama (JP); Nippoh Chemicals Co., Ltd., Tokyo (JP)

(72) Inventors: Junichi Yoshida, Kyoto (JP); Seiji Suga, Kyoto (JP); Kazuhide Kataoka, Okayama (JP); Koji Midorikawa, Isumi (JP); Yuji Hagiwara, Isumi (JP)

(73) Assignees: Japan Science and Technology Agency, Saitama (JP); Nippoh Chemicals Co., Ltd., Tokyo (JP)

( * ) Notice: Subject to any disclaimer, the term of this patent is extended or adjusted under 35 U.S.C. 154(b) by 0 days.

(21) Appl. No.: 13/753,628

(22) Filed: Jan. 30, 2013

(65) Prior Publication Data

US 2013/0144071 A1 Jun. 6, 2013

Related U.S. Application Data

(62) Division of application No. 12/530,274, filed as application No. PCT/JP2008/054184 on Mar. 7, 2008, now Pat. No. 8,383,868.

(30) Foreign Application Priority Data

Mar. 9, 2007 (JP) ................................. 2007-061067
Mar. 9, 2007 (JP) ................................. 2007-061068

(51) Int. Cl.
*C07C 22/00* (2006.01)
(52) U.S. Cl.
USPC .......................................... 570/206; 570/203
(58) Field of Classification Search
None
See application file for complete search history.

(56) References Cited

U.S. PATENT DOCUMENTS

| 5,575,905 | A | 11/1996 | Wistrand et al. | |
| 7,514,589 | B2 * | 4/2009 | Midorikawa et al. | ......... 570/206 |
| 2008/0146853 | A1 | 6/2008 | Midorikawa et al. | |

FOREIGN PATENT DOCUMENTS

| EP | 0 376 858 A2 | 7/1990 |
| EP | 1 837 324 A1 | 9/2007 |
| JP | 05-195272 | 8/1993 |
| JP | 2003-064012 A | 3/2003 |
| JP | 2004-010599 A | 1/2004 |
| WO | 2006/073124 A1 | 7/2006 |

OTHER PUBLICATIONS

International Search Report for corresponding Application No. PCT/JP2008/054184 mailed Jun. 3, 2008.
Form PCT/ISA/237 mailed Jun. 3, 2008.
Larry L. Miller et al., "Iodination with Electrolytically Generated Iodine (I)", Journal of the American Chemical Society, 92:9, May 6, 1970, pp. 2821-2825.
Larry L. Miller et al., "Scope and Mechanism of Aromatic Iodination with Electrochemically Generated Iodine (I)", Journal of the American Chemical Society, 98:6, Mar. 17, 1976, pp. 1515-1519.
Robert Lines et al., "Electrophilic Aromatic Substitution of Positive Iodine Species, Iodination of Deactivated Aromatic Compounds", Acta Chemica Scandinavica B34, 1980, pp. 47-51.
Tatsuya Shono et al., "Aromatic Iodination by Positive Iodine Active Species Generated by Anodic Oxidation in Trimethyl Orthoformate", Tetrahedron Letters, vol. 30, No. 13, 1989, pp. 1649-1650.
Shinkiti Suzuki et al., "Generation of Alkoxycarbenium Ion Pools from Thioacetals and Applications to Glycosylation Chemistry", Organic Letters, vol. 6, No. 21, 2004, pp. 3755-3758.
S. Sharma et al., "A novel and direct selective iodination of toluene to para-iodotoluene using zeolite catalysts", Catalysis Letters, 40, 1996, pp. 257-260.
Roger Adams et al., "*p*-Bromophenol", Organic Syntheses, Coll, vol. 1, 1941, 4 pages.
Mohammad Jafarzadeh et al., "Effective and regioselective iodination of arenes using iron(III) nitrate in the presence of tungstophosphoric acid", Can. J. Chem. 83, 2005, pp. 1808-1811.
Koji Midorikawa et al., "Selective monoiodination of aromatic compounds with electrochemically generated $I^+$ using micromixing", Chem. Commun. 2006, pp. 3794-3796.
"Synthesis and Reaction of Organic Compound (II)", Edited by Chemical Society of Japan, New Courses in Experimental Chemistry vol. 14 (1977), pp. 1150-1153, Maruzen Co., Ltd. with partial English translation.
Office Action dated Jul. 5, 2012 issued for the corresponding European Patent Application No. 08 721 602.4, 5 pages.
WikiEducator, "Chemistry/Iodine Preparation", Chemical/Iodine Preparation—WikiEducator, last modified on Nov. 10, 2008, http://wikieducator.org/Chemistry/Iodine_Preparation, 3 pages.
Office Action mailed Oct. 13, 2011 in co-pending U.S. Appl. No. 12/530,274.

(Continued)

*Primary Examiner* — Sudhakar Katakam
(74) *Attorney, Agent, or Firm* — Renner, Otto, Boisselle & Sklar, LLP

(57) ABSTRACT

A method of the present invention, for producing an iodizing agent, includes the step of electrolyzing iodine molecules in a solution by using an acid as a supporting electrolyte. This realizes (i) a method of producing an iodine cation suitable for use as an iodizing agent that does not require a sophisticated separation operation after iodizing reaction is completed, and (ii) an electrolyte used in the method. Further, a method of the present invention, for producing an aromatic iodine compound, includes the step of causing an iodizing agent, and an aromatic compound whose nucleus has one or more substituent groups and two or more hydrogen atoms, to react with each other under the presence of a certain ether compound. This realizes such a method of producing an aromatic iodine compound that position selectivity in iodizing reaction of an aromatic compound is improved.

5 Claims, No Drawings

(56) References Cited

OTHER PUBLICATIONS

Office Action mailed Jan. 10, 2012 in co-pending U.S. Appl. No. 12/530,274.
Final Office Action mailed Apr. 25, 2012 in co-pending U.S. Appl. No. 12/530,274.
Allowed claims in co-pending U.S. Appl. No. 12/530,274 filed Sep. 8, 2009.
European Office Action mailed Mar. 13, 2013 in corresponding European Application No. 08 721 602.4.
Taylor & Francis, "Elementary General Chemistry", 1941, pp. 421-423.

* cited by examiner

METHOD OF PRODUCING IODIZING AGENT, AND METHOD OF PRODUCING AROMATIC IODINE COMPOUND

CROSS-REFERENCE TO RELATED APPLICATIONS

This application is a divisional of U.S. patent application Ser. No. 12/530,274 filed on Sep. 8, 2009, which is a 371 of PCT/JP2008/054184 filed on Mar. 7, 2008 and claims priority to Japanese Application No. 2007-061067 filed on Mar. 9, 2007 and Japanese Application No. 2007-061068 filed on Mar. 9, 2007, which are hereby incorporated herein by reference in their entirety.

TECHNICAL FIELD

The present invention relates to: a method of producing an iodizing agent; and an electrolyte used in the method. The present invention particularly relates to: a method of producing an iodizing agent by obtaining an iodine cation by electrolyzing iodine molecules; and an electrolyte used in the method. Further, the present invention relates to a method of producing an aromatic iodine compound, particularly, a method of producing an aromatic iodine compound, which is improved in selectivity of a binding position of iodine.

BACKGROUND ART

There has been demand in a wide variety of fields for an aromatic iodine compound in which an iodine atom is bound to a nucleus of an aromatic compound, as an intermediate used for various organic synthesis. In order to produce such an aromatic iodine compound, a method of using an iodine cation has been known. In the method, the iodine cation generated by electrolysis is used as an iodizing agent (see Patent Literature 1 and Non Patent Literatures 1 through 3). The iodine cation is a significantly-effective iodizing agent having high reactivity. For example, Non Patent Literatures 1 and 2 disclose a method of producing an iodine cation by electrolyzing iodine molecules by using metal salt as a supporting electrolyte in an organic solvent (acetonitrile). Further, Non Patent Literatures 1 and 2 disclose that the iodine cation thus obtained was caused to react with various aromatic compounds. Furthermore, Non Patent Literature 3 discloses a method of producing an iodine cation by using quaternary ammonium salt as a supporting electrolyte.

Meanwhile, in such iodizing reaction, a binding position of an iodine atom is determined in accordance with a sort of a substituent group bound to an aromatic compound. That is, the iodine atom is meta oriented, or ortho-para oriented. Here, "meta oriented" means a property that the iodine atom is bound to an aromatic compound in a meta-position with respect to a substituent group, and "ortho-para oriented" means a property that the iodine atom is bound to an aromatic compound in either an ortho-position or a para-position, with respect to a substituent group. In a case where the iodine atom is ortho-para oriented, a product in which iodine is bound in the ortho-position, and another product in which iodine is bound in the para-position, are mixed together in a resultant product of the reaction.

In the iodizing reaction in which iodine is ortho-para oriented as described above, in some cases, the product in which iodine is bound in the ortho-position, and the product in which the iodine is bound in the para-position are obtained at a ratio of substantially 1:1.

However, in recent years, there has been demand for an improvement in selectivity (hereinafter, referred to as "position selectivity" in some cases) of a binding position of an iodine atom in such iodizing reaction. Patent Literature 1 and Non Patent Literature 4 disclose a production method whose purpose is an improvement in selectivity of the binding position of iodine. Specifically, Patent Literature 1 describes that if iodine molecules are subjected to electrolytic oxidation with the use of a carbon electrode, and then toluene is iodized, a compound in which iodine is bound in the para-position can be obtained more in amount than a compound in which iodine is bound in the ortho-position. Further, Non Patent Literature 4 describes that toluene was iodized in a solution containing methyl ester orthoformate having three ester bonds, so that the product in which iodine is bound in the ortho-position, and the product in which iodine is bound in the para-position, were obtained at a ratio of 3:7.

CITATION LIST

Patent Literature 1

Specification of EP Patent No. 0376858 B (Publication Date: Jul. 4, 1990)

Non Patent Literature 1

L. L. Miller, E. P. Kujawa, C. B. Cambell, "Iodation with electrolytically generated iodine (I)" J. Am. Chem. Soc., 92, 2821, (1970)

Non Patent Literature 2

L. L. Miller, B. F. Watkins, "Scope and mechanism of aromatic iodination with electrolytically generated iodine (I)" J. Am. Chem. Soc., 98, 1515, (1976)

Non Patent Literature 3

R. Lines, V. D. Parker, "Electrophilic aromatic substitution by positive iodine species. Iodation of deactivated aromatic compounds" Acta Chem. Scand., B34, p 47, (1980)

Non Patent Literature 4

T. Shono, Y. Matsumura, S. Katoh, K. Ikeda, T. Kamada, "Aromatic iodination by positive iodine active species generated by anodic oxidation in orthoformate" Tetrahedron Letters, 30, 1649, (1989)

SUMMARY OF INVENTION

In order to obtain a target iodine compound, it is necessary to separate a supporting electrolyte from a resultant product after the iodizing reaction is completed. In a case where salt is used as the supporting electrolyte (as in Non Patent Literatures 1 through 3), column chromatography is required depending on a sort of salt. It is difficult to apply a separation operation employing the column chromatography to industrial production. This has been one of obstacles to industrialization of the method of producing an aromatic compound by using an iodine cation generated by electrolysis. For this reason, there has been demand for development of a method of producing an iodizing agent, which method (i) does not require a sophisticated separation operation for isolation of a target iodine compound after the iodizing reaction is completed, and (ii) realizes industrial production of the target iodine compound.

Further, the inventors of the present invention confirmed that with any one of the methods disclosed in Patent Literature 1 and Non Patent Literature 4, it is not possible to improve a generation rate of an aromatic iodine compound in which iodine is bound to an aromatic compound in the para-position. Therefore, there has been demand for development of a method of producing an aromatic iodine compound, which method realizes iodizing reaction in which position selectivity is improved.

The present invention is made in view of the problems. An object of the present invention is to realize: a method of producing an iodizing agent, in which method (a) an iodine cation is obtained by electrolysis, and (b) in a case where the iodine cation thus obtained is used as an iodizing agent, it becomes unnecessary to carry out a sophisticated separation operation after iodizing reaction is completed; an electrolyte used in the method; and a method of producing an aromatic iodine compound, in which method position selectivity of iodine is improved.

A method of the present invention, for producing an iodizing agent, includes the step of electrolyzing iodine molecules by using an acid as a supporting electrolyte.

In the method of the present invention, for producing an iodizing agent, the acid is preferably at least one selected from the group consisting of: sulphonic acids and phosphoric acids, the sulphonic acids being represented by the following General Formula (1):

$$R^1SO_3H \quad (1)$$

(where: $R^1$ is one selected from the group consisting of a hydroxyl group, a $C_{1-6}$ alkyl group, a phenyl group, and a naphthyl group; in the alkyl group, a hydrogen atom may be substituted with a fluorine atom; the phenyl group and the naphthyl group may have a substituent group), and the phosphoric acids being represented by the following General Formula (2):

(where: $R^2$ and $R^3$ are, identically or differently, a hydrogen atom, a $C_{1-10}$ alkyl group, or a phenyl group; and the phenyl group may have a substituent group). It should be noted that, in the present invention, examples of the phosphoric acids include ester phosphate.

In the method of the present invention, for producing an iodizing agent, the solution preferably contains an organic solvent.

In the method of the present invention, for producing an iodizing agent, the organic solvent is preferably at least one selected from the group consisting of aliphatic nitrile, alcohol, a chlorinated solvent, aliphatic amide, cyclic ether, and nitromethane.

The method of the present invention, for producing an iodizing agent, employs an acid as a supporting electrolyte. Therefore, in a case where an iodine cation is used as an iodizing agent to synthesize an iodine compound, it is possible to easily separate the supporting electrolyte after reaction is completed. The inventors of the present invention found, as a result of diligent study, that in place of salt, an acid can be used as a supporting electrolyte in electrolysis of the iodine molecules. An acid can be removed by, for example, neutralization reaction, without separation process by column chromatography. In other words, with the present invention, it is possible to obtain an iodine cation that does not require a sophisticated separation operation after the iodizing reaction is completed. The iodine cation obtained by the method of the present invention is suitable for use as an iodizing agent for various compounds.

Non Patent Literature 3 discloses a method in which iodine molecules are electrolyzed in an organic solvent to which trifluoroacetic acid is added, so as to obtain an iodine cation that can be used for iodizing various aromatic compounds. However, with the method disclosed in Non Patent Literature 3, trifluoroacetic acid does not function as a supporting electrolyte.

An electrolyte of the present invention contains an acid used as a supporting electrolyte, and iodine molecules, the acid having a concentration of not less than 0.01 mol/L but not more than 19.0 mol/L.

In the electrolyte of the present invention, a concentration of the iodine molecules is preferably not less than 0.1 percent by mass but not more than 50 percent by mass. It should be noted that, in the present invention, "electrolyte" is a solution which contributes to the electrolysis without having any change. Therefore, in a case where a solution out of the range described above is prepared, and from the solution, a solution within the range described above is obtained by a known concentration preparing process (dilution or concentration) before electricity is applied, such a solution is also included in a range of the electrolyte of the present invention.

The electrolyte of the present invention is preferably used as an electrolyte for obtaining an iodine cation by electrolyzing iodine molecules.

By carrying out the electrolysis by use of the electrolyte of the preset invention, it is possible to obtain the iodine cation which is suitable for use as an iodizing agent for various compounds.

Further, the inventors of the present invention found, as a result of diligent study on production of an aromatic iodine compound in which position selectivity of iodine is improved, that by causing an iodine cation and an aromatic compound whose nucleus has one or more substituent groups and two or more hydrogen atoms, to react with each other under the presence of at least one selected from the group consisting of a certain acyclic ether compound and a certain cyclic ether compound, it is possible to improve the selectivity of a binding position of iodine with respect to a substituent group of an aromatic compound.

A method of the present invention, for producing an aromatic iodine compound, includes the step of (a) causing an iodizing agent, and an aromatic compound whose nucleus has one or more substituent groups and two or more hydrogen atoms, to react with each other under the presence of at least one selected from the group consisting of cyclic or acyclic ether compounds being represented by the following General Formula (3):

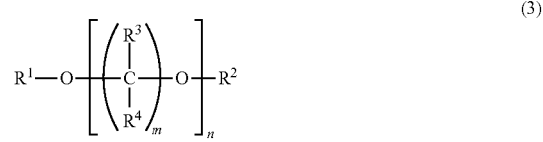

(where m is any integer in a range from 2 to 6; n is an integer not less than 1; $R^1$ and $R^2$ are, identically or differently, a hydrogen atom or a $C_{1-10}$ alkyl group; $R^3$ and $R^4$ are, identically or differently a hydrogen atom or a $C_{1-10}$ alkyl group).

Further, in the present invention, the alkyl group may be substituted, and includes, for example, an alkyl group having a thioether bond.

In the method of the present invention, for producing an aromatic iodine compound, the cyclic ether compound preferably contains a $C_{3-12}$ ring.

In the method of the present invention, for producing an aromatic iodine compound, the iodizing compound is preferably an iodine cation.

The method of the present invention, for producing an aromatic iodine compound, preferably further includes the steps of: separating a solid reaction product from a reaction solution obtained in a reaction step described above; and recrystallizing the reaction product thus separated from the reaction solution.

The method of the present invention, for producing an aromatic compound, preferably further includes the step of isolating a reaction product by carrying out distillation process with respect to a reaction solution obtained in a reaction step described above.

A system of the present invention, for producing an aromatic iodine compound includes: a first tank for storing an aromatic compound having one or more substituent groups; a second tank for storing at least one selected from the group consisting of cyclic or acyclic ether compounds; and a third tank for storing an iodizing agent.

With a method of the present invention, for producing an aromatic iodine compound, it is possible to improve selectivity of a binding position of an iodine atom by carrying out iodizing reaction under the presence of a certain acyclic ether compound and a certain cyclic ether compound. Therefore, with the preset invention, it is possible to efficiently produce a single product by decreasing a generation rate of an isomer.

Additional objects, features, and strengths of the present invention will be made clear by the description below. Further, the advantages of the present invention will be evident from the following explanation in reference to the drawings.

DESCRIPTION OF EMBODIMENTS

[1. Method of Producing Iodizing Agent]

The following description explains details of a method of the present invention, for producing an iodizing agent. The method of the present invention, for producing an iodizing agent, includes the step of electrolyzing iodine molecules in a solution containing an acid which can function as a supporting electrolyte.

1-1. Electrolyte

An electrolyte of the present invention contains an acid and iodine molecules.

(Solvent)

A solvent dissolves the iodine molecules and the acid, so as to contribute to electrolysis of the iodine molecules. Such a solvent is preferably an organic solvent. The organic solvent may be at least one selected from the group consisting of aliphatic nitrile, alcohol, a chlorinated solvent, aliphatic amide, cyclic ether, and nitromethane. Specifically, examples of the organic solvent include: acetonitrile; propionitrile; butyronitrile; isobutyronitrile; valeronitrile; isovaleronitrile; pivalonitrile; hexanenitrile; methanol; ethanol; propanol; isopropanol; butanol; isobutanol; tert-butanol; chloroform; dichloromethane; carbon tetrachloride; 1,2-dichloroethane; 1,1,1-trichloroethane; 1,1,2-trichloroethane; N,N-dimethylformamide; N,N-dimethylacetamide; N-methylpyrrolidone; N-methylpiperidone; tetrahydrofuran; 1,4-dioxane; tetrahydropyran; and nitromethane.

(Acid)

The method of the present invention, for producing an iodizing agent, employs an acid as a supporting electrolyte. In descriptions of the present specification, the "acid" means an acid that becomes dissociated into ions in a solvent, and plays a role of leading, into the solvent, electricity which is necessary for the electrolysis.

The acid is preferably at least one selected from the group consisting of: sulphonic acids and phosphoric acids, the sulphonic acids being represented by the following General Formula (1):

$$R^1SO_3H \qquad (1),$$

(where: $R^1$ is one selected from the group consisting of a hydroxyl group, a $C_{1-6}$ alkyl group, a phenyl group, and a naphthyl group; in the alkyl group, a hydrogen atom may be substituted by a fluorine atom; and the phenyl group and the naphthyl group may include a substituent group), and the phosphoric acids being represented by the following General Formula (2):

$$R^2O-\overset{\overset{O}{\|}}{\underset{R^3O}{P}}-OH \qquad (2)$$

(where: $R^2$ and $R^3$ are, identically or differently, a hydrogen, a $C_{1-10}$ alkyl group, or a phenyl group; and the phenyl group may have a substituent group).

Examples of the sulphonic acids include: sulfuric acid; methanesulphonic acid; ethanesulphonic acid; benzenesulphonic acid; p-toluenesulphonic acid; and trifluoromethanesulphonic acid. Examples of the phosphoric acids include: phosphoric acid; methylphosphoric acid; butylphosphoric acid; isodecylphosphoric acid; 2-ethylhexylphosphoric acid; and phenylphosphoric acid.

A concentration of an acid in the electrolyte is not less than 0.01 mol/L but not more than 19.0 mol/L, preferably not less than 0.05 mol/L but not more than 10.0 mol/L, more preferably, not less than 0.1 mol/L but not more than 5.0 mol/L. In a case where the concentration of the acid is less than 0.01 mol/L, the acid cannot cause electricity to flow in the solution, that is, the acid cannot function as the supporting electrolyte. Further, in a case where the concentration of the acid is more than 19.0 mol/L, it becomes difficult to prepare the concentration of the acid.

(Iodine Molecules)

In the method of the present invention, for producing an iodizing agent, iodine molecules are electrolyzed. This eliminates the need to carry out separation process with respect to a metal ion derived from an iodine metal compound, after iodizing reaction is completed. Further, in a case where the iodine metal compound is used, a monovalent iodine anion exists in the solvent. For this reason, in order to obtain the iodine cation, it is necessary to extract two electrons. On the other hand, in a case where the iodine molecules are used, it is possible to generate the iodine cation by extracting only one electron. This allows a reduction in amount of electricity for the electrolysis. A content ratio of the iodine molecules in the electrolyte is not less than 0.1 percent by mass but not more than 50 percent by mass, preferably not less than 0.5 percent by mass but not more than 25 percent by mass, more preferably 1.0 percent by mass but not more than 10 percent by mass.

1-2. Production of Iodine Cation

The electrolysis is carried out with the use of the electrolyte described above, so as to obtain the iodine cation in accordance with the following Reaction Formula (4).

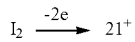

(4)

The electrolysis can be carried out with the use of an electrolyzing device in which two rooms are provided for an anode and a cathode separately and respectively, for example. In the room for the anode, the iodine molecules, the supporting electrolyte, and the solvent are provided, and in the room for the cathode, the supporting electrolyte and the solvent are provided. It is preferable that the reaction takes place while these thus provided are agitated. The reaction can be carried out at a temperature of not less than −100° C. but not more than 100° C., preferably not less than −40° C. but not more than 40° C., more preferably not less than −20° C. but not more than 25° C. In the temperature range described above, it is possible to successfully obtain the iodine cation. The amount of electricity for the electrolysis is preferably not less than 0.5 F but not more than 5.0 F, per 1 mol of the iodine molecules. This makes it possible to obtain a solution containing the iodine cation (hereinafter, referred to as an "iodine cation solution", in some cases) in the room for the anode. In a case where the amount of electricity is less than 0.5 F, it is impossible to carry out the electrolysis, and in a case where the amount of electricity is more than 5.0 F, there is a risk that the solvent is oxidized apart from iodine, or the iodine cation is excessively oxidized, for example.

Examples of the electrode include: a metal (copper, silver, gold, or platinum, for example) electrode; an electrode coated with a metal (copper, silver, gold, or platinum, for example); a corrosion-resisting alloy electrode (stainless steel, or HASTELLO® for example); and a carbon electrode (graphite, or diamond, for example). A platinum electrode is particularly preferable.

1-3. Production of Aromatic Iodine Compound

The iodine cation obtained in the reaction described above can be used to iodize various compounds. Particularly, the iodine cation is suitable for use as an iodizing agent for causing iodine to be bound to a nucleus of an aromatic compound.

The following description explains an example of iodization with the use of the iodine cation. In the example, the iodine cation and an aromatic compound are caused to react with each other in a solvent so as to produce an aromatic iodine compound. This reaction can be represented by the following Reaction Formula (5). Reaction Formula (5) is for a case where toluene is used as the aromatic compound.

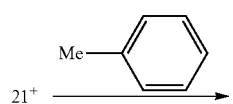

(5)

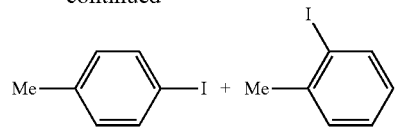

The aromatic iodine compound can be obtained in such a manner that (i) an iodine cation solution is added to a solution in which an aromatic compound is dissolved, and (ii) the resultant solution is agitated until the reaction is completed. In the present invention, the aromatic compound means a compound showing an aromatic character, and may have either an isocyclic ring or a heterocyclic ring. The aromatic compound having the isocyclic ring may be a $C_{6-12}$ compound, such as a benzene ring, and a naphthalene ring.

The aromatic compound having the heterocyclic ring may be a compound having a five-membered or six-membered hetero ring having at least one (generally one to three) hetero atom selected from the group consisting of an oxygen atom, a nitrogen atom, and a sulfur atom, for example. In this case, the hetero ring may constitute a fused ring. Specifically, examples of the compound having the heterocycle encompass: a compound containing an oxygen atom as a hetero atom (furans, for example); a compound containing a sulfur atom as a hetero atom (thiophenes, thiazoles, or isothiazoles, for example); and a compound containing a nitrogen atom as a hetero atom (pyrroles, pyrazoles, imidazoles, triazoles, or pyridines, for example).

Specifically, examples of the aromatic compound include: toluene; ethylbenzene; propylbenzene; isopropylbenzene; tert-butylbenzene; o-xylene; m-xylene; p-xylene; biphenyl; naphthalene; m-terphenyl; p-terphenyl; phenol; anisole; thiophene; aniline; chlorobenzene; bromobenzene; iodobenzene; p-chlorotoluene; o-chlorotoluene; p-chlorophenol; 4-methylanisole; 2-methylanisole; o-dimethoxybenzene; m-dimethoxybenzene; and p-dimethoxybenzene.

In this case, the solvent for dissolving the aromatic compound may be: acetonitrile; propionitrile; butyronitrile; isobutyronitrile; valeronitrile; isovaleronitrile; pivalonitrile; hexane; methylcyclohexane, heptane; octane; decane; dodecane; methanol; ethanol; propanol; isopropanol; butanol; isobutanol; tert-butanol; diethyl ether; diisopropyl ether; tert-butylmethyl ether; dibutyl ether; cyclopentylmethyl ether; 1,2-dimethoxyethane; 1,2-diethoxyethane; diethylene glycol dimethyl ether; diethylene glycol diethyl ether; diethylene glycol monomethyl ether; diethylene glycol monoethyl ether; triethylene glycol monomethyl ether; triethylene glycol monoethyl ether; tetraethylene glycol dimethyl ether; tetraethylene glycol diethyl ether; tetraethylene glycol monomethyl ether; tetraethylene glycol diethyl ether; ethylene glycol; ethylene glycol monomethyl ether; ethylene glycol monoethyl ether; polyethylene glycol; tetrahydrofuran; 1,4-dioxane; tetrahydropyran; dichloromethane; chloroform; carbon tetrachloride; 1,2-dichloroethane; 1,1,1-trichloroethane; 1,1,2-trichloroethane; nitromethane; and pentafluorobenzoic acid, for example.

Further, in this synthesis, it is possible to improve selectivity of the binding position of iodine by causing the iodine cation and an aromatic compound whose nucleus has at least one substituent group and at least two hydrogen atoms, to react with each other under the presence of a certain ether compound.

The aromatic compound may have an electron-donating substituent group. Examples of such an aromatic compound include: toluene; o-xylene; m-xylene; 2-chlorotoluene;

3-methoxyphenol; 2-methylanisole; 3-methylanisole; ethylbenzene; cumene; and tert-butylbenzene.

It is considered that an ether compound and an amide compound play a role of sterically preventing iodine from being bound in an ortho-position in a solvent. In this case, the ether compound and the amide compound may be added to a solution in which the aromatic compound is dissolved, or, in a case where the aromatic compound is soluble in the ether compound and the amide compound, the ether compound and the amide compound themselves may be used as the solvent.

The ether compound may be either an acyclic ether compound or a cyclic ether compound. The acyclic ether compound used in the method of the present invention, for producing the aromatic iodine compound, includes at least two ether-bonds, and has a carbon chain having 2 or more carbon atoms, between an oxygen atom at one ether bond, and an oxygen atom at another ether bond. An example of such an acyclic ether compound may be a compound represented by the following General Formula (6)

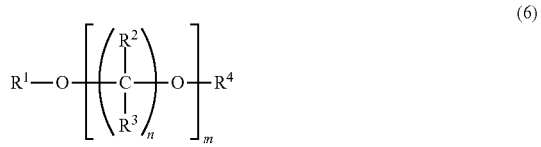

(6)

(where: m is an integer not less than 1; n is an integer not less than 2; $R^1$ and $R^4$ are, identically or differently, a hydrogen atom or a $C_{1-3}$ alkyl group; the alkyl group may be substituted by an alkoxy group; $R^2$ and $R^3$ are, identically or differently, a hydrogen atom or a $C_{1-3}$ alkyl group).

Specifically, examples of the compound represented by General Formula (6) encompass: 1,2-dimethoxyethane; 1,2-diethoxyethane; diethylene glycol dimethyl ether; diethylene glycol diethyl ether; diethylene glycol monomethyl ether; diethylene glycol monoethyl ether; triethylene glycol dimethyl ether; triethylene glycol diethyl ether; triethylene glycol monomethyl ether; triethylene glycol monoethyl ether; tetraethylene glycol dimethyl ether; tetraethylene glycol diethyl ether; tetraethylene glycol monomethyl ether; tetraethylene glycol monoethyl ether; ethylene glycol; ethylene glycol monomethyl ether; ethylene glycol monoethyl ether; and polyethylene glycol.

The cyclic ether compound is a cyclic compound having one or more ether bonds. The cyclic ether compound may be tetrahydrofuran; crown ether; 1,4-dioxane; tetrahydropyran; or 1,3,5-trioxane, for example.

Further, in a case where the ether compound is added, an amount of the ether compound added to the solution is preferably not less than 0.1 times but not more than 10.0 times more than the iodine cation solution, more preferably not less than 0.5 times but not more than 1.5 times more than the iodine cation solution. In a case where the amount is too small, there is no improvement in selectivity, and in a case where the amount is too large, there is a reduction in yield of iodization.

The iodine cation solution obtained by the electrolysis is added to a solution in which the aromatic compound is dissolved, and the resultant solution is continuously agitated. In this manner, the reaction can be completed. At this point, the reaction preferably takes place at a temperature of not less than −40° C. but not more than 150° C. A reaction solution thus obtained is subjected to a known separation operation (extract operation, liquid separation operation), so that a target reaction product is isolated.

The method of the present invention, for producing an iodizing agent, employs an acid as the supporting electrolyte. Therefore, in a case where an iodine compound is synthesized by using the iodine cation as an iodizing agent, it is possible to easily separate the supporting electrolyte from a reaction solution after reaction is completed. The inventors of the present invention found, as a result of diligent study, that in place of salt, an acid can be used in electrolyzing iodine molecules. With the use of an acid, it is not necessary to carry out separation process by the column chromatography, and an acid can be removed by, for example, neutralization reaction. For this reason, with the present invention, it is possible to obtain an iodine cation that does not require a sophisticated separation operation after reaction is completed in a case where the iodine cation is used as an iodizing agent.

[2. Method of Producing Aromatic Iodine Compound]

The following description explains details of the method of the present invention, for producing an aromatic iodine compound. The method of the present invention, for producing an aromatic iodine compound, includes the step of causing an iodizing agent and an aromatic compound whose nucleus has one or more substituent groups and two or more hydrogen atoms, to react with each other under the presence of a certain ether compound.

2-1. Iodizing Agent

First, the following description explains the iodizing agent. The iodizing agent is preferably an iodine cation, for example.

Here, the following description explains a method of producing the iodine cation. The iodine cation can be obtained by, for example, electrolyzing at least one selected from the group consisting of iodine molecules and an iodine metal compound (iodine anion) in a solution containing a supporting electrolyte. In order to obtain such an iodine cation, firstly, the electrolyte is prepared. The electrolyte is a solution containing (i) a supporting electrolyte, and (ii) iodine molecules or an iodine metal compound.

(Solvent)

A solvent constituting the electrolyte is a solvent that can dissolve (i) iodine molecules or an iodine metal compound, and (ii) a supporting electrolyte, so as to contribute to the electrolysis. Such a solvent is preferably an organic solvent. The organic solvent may be one selected from the group consisting of aliphatic nitrile, alcohol, a chlorinated solvent, aliphatic amide, cyclic ether, and nitromethane. Specifically, examples of the organic solvent encompass: acetonitrile; propionitrile; butyronitrile; isobutyronitrile; valeronitrile; isovaleronitrile; pivalonitrile, hexanenitrile; methanol; ethanol; propanol; isopropanol; butanol; isobutanol; tert-butanol; chloroform; dichloromethane; carbon tetrachloride; 1,2-dichloroethane; 1,1,1-trichloroethane; 1,1,2-trichloroethane; N,N-dimethylformamide; N,N-dimethylacetamide; N-methylpyrrolidone; N-methylpiperidone; tetrahydrofuran; 1,3-dioxane; 1,4-dioxane; 1,3,5-trioxane; tetrahydropyran; and nitromethane.

(Supporting Electrolyte)

The supporting electrolyte is preferably an acid or salt. The supporting electrolyte becomes dissociated into ions in the solvent, and plays a role of introducing electricity to the solvent. In a case where salt is used, examples of the supporting electrolyte include: $(nBu)_4NBF_4$; $Et_4NBF_4$; $NaClO_4$; $LiBF_4$; $LiClO_4$; $(nBu)_4NClO_4$; $Et_4NClO_4$; $LiCl$; $(nPr)_4NClO_4$; $Mg(ClO_4)_2$; $(nBu)_4NCl$; $(nBu)_4NBr$; $(nBu)_4NI$; $Et_4NCl$; $Et_4NBr$; $Et_4NI$; $(nPr)_4NBr$; $(nPr)_4NI$; and $KOH$.

In a case where an acid is used, the supporting electrolyte may be at least one selected from the group consisting of sulfuric acid, methanesulphonic acid, benzenesulphonic acid, p-toluenesulphonic acid, and phosphoric acid. The supporting electrolyte is preferably an acid. With the use of an acid, there is an advantage that it is unnecessary to carry out the separation operation by the column chromatography, in a case where the supporting electrolyte is removed after the iodizing reaction is completed.

In the case of an acid, a concentration of the acid in the electrolyte is not less than 0.01 mol/L but not more than 19.0 mol/L, preferably not less than 0.05 mol/L but not more than 10.0 mol/L, more preferably not less than 0.1 mol/L but not more than 5.0 mol/L. In a case where the concentration of the acid is lower than 0.01 mol/L, it is impossible to cause the electricity to flow in the solution. That is, the acid cannot play the role of the supporting electrolyte. Further, in a case where the concentration of the acid is higher than 19.0 mol/L, there is a problem that it is difficult to prepare the concentration of the acid.

(Iodine Molecules or Iodine Metal Compound)

In the method of the present invention, for producing the iodine cation, the iodine molecules or the iodine metal compound is electrolyzed. In a case where the iodine molecules are used, a content ratio of the iodine molecules in the electrolyte is not less than 0.1 percent by mass but not more than 50 percent by mass, preferably not less than 0.5 percent by mass but not more than 25 percent by mass, more preferably not less than 1.0 percent by mass but not more than 10 percent by mass. In a case where an amount of the iodine molecules in the electrolyte is within the range described above, the iodine cation can be successfully produced without a reduction in productivity. Examples of the iodine metal compound include: potassium iodide; sodium iodide; lithium iodide; ammonium iodide; barium iodide; copper iodide; lead iodide; and rubidium iodide.

A starting compound for obtaining the iodine cation is preferably the iodine molecules. Unlike the iodine metal compound, the iodine molecules do not exist as an ion in the solvent. Therefore, with the use of the iodine molecules, it is possible to generate the iodine cation by extracting only one electron. On the other hand, since the iodine metal compound exists as a monovalent iodine anion in the solvent, it is necessary to extract two electrons in order to obtain the iodine cation with the use of the iodine metal compound. In other words, there is an advantage that, by electrolyzing the iodine molecules, the amount of electricity becomes less required for the electrolysis. Further, if the iodine metal compound (sodium iodide, or potassium iodide, for example) is used as the starting compound, a metal ion is mixed with a resultant iodine cation solution. However, if the iodine molecules are used as the starting compound, it is possible to avoid such a state. Therefore, it is possible to obtain the iodine cation that does not require separation operation employing the column chromatography.

(Electrolysis).

The electrolysis is carried out with the use of the electrolyte described above, so as to obtain the iodine cation in accordance with the following Reaction Formula (4). The following Reaction Formula (4) is for a case where the iodine molecules are oxidized by the electrolysis.

(4)

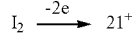

This electrolysis can be carried out, for example, with the use of an electrolytic cell in which two rooms are provided for the anode and the cathode, respectively and independently. Into the room for the anode, the iodine molecules or the iodine metal compound are/is provided, and into the room for the cathode, the supporting electrolyte and the solvent are provided. Further, the reaction can be carried out at a temperature of not less than −100° C. but not more than 100° C., preferably at a temperature of not less than −40° C. but not more than 40° C., more preferably at a temperature of not less than −20° C. but not more than 25° C. The iodine cation can be successfully obtained at a temperature in the range described above. The amount of the electricity used in the electrolysis is preferably not less than 0.5 F but not more than 5.0 F, per 1 mol of the iodine molecules. This makes it possible to produce a solution containing the iodine cation (hereinafter, referred to as "iodine cation solution" in some cases) in the room for the anode. In a case where the amount of the electricity is less than 0.5 F, it is impossible to carry out the electrolysis, and in a case where the amount of the electricity is more than 5.0 F, there is a risk that the solvent apart from iodine is oxidized, or the iodine cation is excessively oxidized, for example.

Examples of the electrode include: a metal electrode (copper, silver, gold, or platinum, for example); an electrode coated with a metal (copper, silver, gold, or platinum, for example); a corrosion-resisting alloy electrode (stainless steel, or HASTELLOY®, for example); and a carbon electrode (graphite, or diamond, for example). The platinum electrode is particularly preferable.

In addition to the aforementioned method of producing the iodine cation by carrying out the electrolysis, the following method can be used to obtain the iodine cation. At least one selected from the group consisting of N-iodosuccinimide, N,N-diiodo-5,5-dimethylhydantoin, and bispyridineiodonium tetrafluoroborate is dissolved in the solvent, and an acid (such as tetrafluoroboric acid or trifluoromethansulphonic acid) is added to the resultant solution. This makes it possible to easily produce the iodine cation.

Further, other than the acids described above, an oxidizing agent may be added to the resultant solution so as to produce the iodine cation. Examples of the oxidizing agent encompass: sodium hypochlorite, sodium chlorite, sodium chlorate, sodium perchlorate, sodium hypobromite, sodium bromate, sodium periodate, sodium iodate, chlorine, bromine, ammonium persulfate, hydrogen peroxide, and acetyl hydroperoxide.

2-2. Production of Aromatic Iodine Compound

Next, the iodine cation obtained by the electrolysis and an aromatic compound having one or more substituent groups are caused to react with each other. The following description explains a method of the present invention, for producing an aromatic iodine compound. The explanations are made for a case where the aromatic compound is toluene, for example.

The aromatic iodine compound of the present invention is produced in accordance with the following Reaction Formula (5):

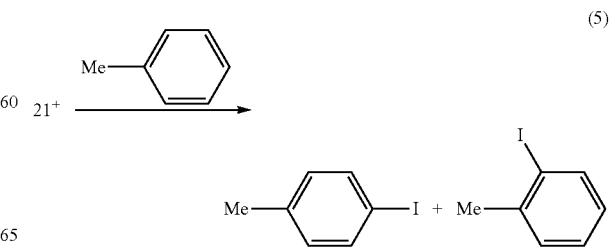

An aromatic compound used here has a nucleus to which one or more substituent groups and two or more hydrogen atoms are bound. In the present invention, the aromatic compound is a compound showing an aromatic characteristic, and may have either an isocyclic ring or a heterocyclic ring (nucleus). The aromatic compound having the isocyclic ring may be, for example, a compound having a $C_{6-12}$ isocyclic ring, such as a benzene ring, or a naphthalene ring.

The aromatic compound having the heterocyclic ring may be, for example, a compound having a five-membered or six-membered heterocycle having at least one (generally one to three) hetero atom selected from the group consisting of an oxygen atom, a nitrogen atom, and a sulfur atom. In this case, the heterocycle may constitute a fused ring. Specifically, examples of the compound having the heterocycle encompass: furans each of which includes an oxygen atom as the hetero atom; thiophenes each of which includes a sulfur atom as the hetero atom; thiazoles each of which includes a sulfur atom as the hetero atom; isothiazoles each of which includes a sulfur atom as the hetero atom; pyrroles each of which includes a nitrogen atom as the hetero atom; pyrazoles each of which includes a nitrogen atom as the hetero atom; imidazoles each of which includes a nitrogen atom as the hetero atom; triazoles each of which includes a nitrogen atom as the hetero atom; and pyridines each of which includes a nitrogen atom as the hetero atom.

Specifically, the aromatic compound preferably has one or more substituent groups. The substituent group is preferably an electron-donating group, in particular. Examples of such an aromatic compound encompass: toluene; o-xylene; m-xylene; fluorobenzene; chlorobenzene; iodobenzene; phenol; o-cresol; m-cresol; anisole; aniline; N,N-dimethyaniline; o-toluidine; m-toluidine; 2-chlorotoluene; 3-chlorotoluene; 2-bromotoluene; 3-bromotoluene; 2-fluorotoluene; 3-fluorotoluene; 2-iodotoluene; 3-iodotoluene; 2-methoxyphenol; 3-methoxyphenol; 2-methylanisole; 3-methylanisole; 1,2-dimethoxybenzene; 1,3-dimethoxybenzene; ethylbenzene; propylbenzene; benzyl chloride; benzyl bromide; cumene; tert-butylbenzene; biphenyl; and p-terphenyl.

In this case, the solvent for dissolving the aromatic compound may be: acetonitrile; propionitrile; butyronitrile; isobutyronitrile; valeronitrile; isovaleronitrile; pivalonitrile; hexane; methylcyclohexane; heptane; octane; decane; dodecane; methanol; ethanol; propanol; isopropanol; butanol; isobutanol; tert-butanol; diethyl ether; diisopropyl ether; tert-butylmethyl ether; dibutyl ether; cyclopentylmethyl ether; 1,2-dimethoxyethane; tetrahydrofuran; 1,4-dioxane; tetrahydropyran; dichloromethane; chloroform; carbon tetrachloride; 1,2-dichloroethane; 1,1,1-trichloroethane; 1,1,2-trichloroethane; nitromethane; and pentafluoro benzoic acid. Further, the solvent may be an ether compound (which will be described later).

In the present invention, the reaction between the iodizing agent and the aromatic compound takes place under the presence of a certain ether compound. The certain ether compound presumably plays a role of inhibiting iodine from being bound in the ortho-position in the solvent. In the present invention, the certain ether compound may be added to a solution in which the aromatic compound is dissolved, or, in a case where the aromatic compound is soluble in the certain ether compound, the certain ether compound itself may be used as the solvent.

(Ether Compound)

The ether compound may be at least one selected from the group consisting of cyclic or acyclic ether compounds being represented by General Formula (3):

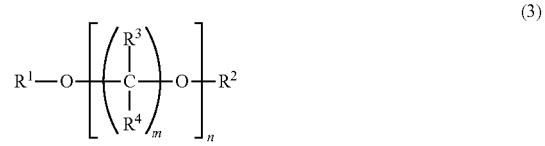

(where: m is any integer in a range from 2 to 6; n is an integer not less than 1; $R^1$ and $R^2$ are, identically or differently, a hydrogen atom or a $C_{1-10}$ alkyl group; $R^3$ and $R^4$ are, identically or differently, a hydrogen atom or a $C_{1-10}$ alkyl group).

Specifically, examples of the ether compound represented by General Formula (3) encompass: 1,2-dimethoxyethane; 1,2-diethoxyethane; diethyleneglicoldimethyl ether; diethyleneglicoldiethyl ether; diethyleneglicolmonomethyl ether; diethyleneglicolmonoethyl ether; triethyleneglicolmonomethyl ether; triethyleneglicolmonoethyl ether; triethyleneglicoldimethyl ether; triethyleneglicoldiethyl ether; tetraethyleneglicoldimethyl ether; tetraethyleneglicoldiethyl ether; tetraethyleneglicolmonomethyl ether; tetraethyleneglicolmonoethyl ether; ethyleneglicol; ethyleneglicolmonomethyl ether; ethyleneglicolmonoethyl ether; and polyethyleneglicol.

The cyclic ether compound is a cyclic compound having one or more ether bonds. Examples of the cyclic ether compound encompass: ethylene oxide; triethylene oxide; tetrahydrofuran; crown ether; 1,4-dioxane; 1,3-dioxane; tetrahydropyran; and 1,3,5-trioxane.

Further, in a case where the ether compound is added to the solution, an amount of the ether compound added to the solution is preferably 0.1 to 10.0 times more than a content of the iodizing agent solution, more preferably 0.5 to 1.5 times more than the content of the iodizing agent solution. In a case where the amount is less than 0.1 times the iodizing agent solution, there is no improvement in selectivity, and in a case where the amount is more than 10.0 times the iodizing agent solution, there may be a reduction in yield of the iodization.

To the solution in which the aromatic compound is dissolved, the iodine cation solution obtained by the electrolysis is added, and the resultant solution is agitated continuously. Thereby, the reaction is completed. At this time, the reaction preferably takes place at a temperature of not less than −40° C. but not more than 100° C. The resultant reaction solution is subjected to the separation operation (extract operation, liquid separation operation), so as to isolate the target reaction product. Further, the reaction preferably takes place at a temperature of not less than −40° C. but not more than 0° C. By carrying out the reaction at a temperature in the range, the position selectivity can be further improved.

After that, the reaction product is isolated by a known separation operation (extracting, liquid separating, or the column chromatography, for example).

Further, it is possible to increase a degree of purity of the reaction product thus obtained by recrystallizing the reaction product. Specifically, it is preferable that (i) the resultant crude product is dissolved in an alcohol (such as methanol, ethanol, propanol, isopropanol, and butanol), (ii) deposition of a crystal is carried out at a temperature of not less than −80° C. but not more than 0° C., and then (iii) this procedure is repeated several times. With this method, it is possible to increase the degree of purity to approximately 98%. By carrying out the process within the temperature range, it is possible to carry out the recrystallization to obtain a high purity product.

Further, the operation to increase the degree of purity of the product is not limited to the recrystallization, and a high purity reaction product can be isolated by carrying out distillation process with respect to the resultant reaction solution.

According to the method of the present invention, for producing an aromatic iodine compound, it is possible to improve selectivity of a binding position of iodine by causing, in iodizing process, an iodine cation and an aromatic compound to react with each other under the presence of a certain ether compound. Therefore, it becomes possible to efficiently produce the target aromatic iodine compound.

Further, the certain ether compound used in the method of the present invention, for producing an aromatic iodine compound, is stable in a solvent, so that it is easy to handle the certain ether compound. Therefore, it is possible to carry out, with high reproducibility, the iodizing reaction in which position selectivity is improved. Thereby it is possible to provide a production method suitable for industrialization.

Furthermore, the method of the present invention, for producing an aromatic iodine compound, has an advantage that, by using, as an iodizing agent, the iodine cation obtained by electrolysis for which an acid is used as a supporting electrolyte, the supporting electrolyte can be removed easily after the reaction is completed.

EXAMPLES

The following description explains examples of the present invention. It should be noted that the present invention is not limited to the following examples.

1. Production of Iodizing Agent

Example 1

(Production of Iodine Cation)

Production of an iodine cation was carried out with the use of an H-type 2-room electrolytic cell under an anhydrous condition. At that time, a glass filter (G4) was used as a diaphragm. As an anode electrode and a cathode electrode, platinum plates (30 mm×20 mm) were used. The electrolytic cell was dried under reduced pressure, and then was filled with nitrogen atmosphere. Then, 13 mL of an acetonitrile solution containing 2.0M of sulfuric acid was provided in a cathode room, and 13 mL of acetonitrile solution containing 2.0M of sulfuric acid, and 127 mg (0.500 mmol) of iodine were provided in an anode room. After that, the electrolytic cell was cooled down to 0° C. While the anode room and the cathode room were agitated with the use of a magnetic stirrer, electrolysis was carried out with a constant current (20 mA) at 0° C. By applying 2.0 F/mol electricity, an iodine cation solution was obtained from the anode room.

(Production of Aromatic Iodine Compound)

Next, 12.5 ml of the iodine cation solution thus obtained was added to 2.5 ml of an acetonitrile solution containing 92 mg (1.0 mmol) of toluene. At this point, a temperature of a reaction solution was 0° C. The reaction solution was agitated for a half hour. After reaction was completed, 13 mL of 4N aqueous sodium hydroxide was added to the reaction solution at 0° C., so as to neutralize the reaction solution. Then, the resultant solution was diluted with 20 mL of ether. A resultant reaction mixture was put into a separatory funnel, so that the mixture was separated into an organic layer and an aqueous layer. The aqueous layer was extracted with ether, and the organic layer was washed with a saturated saline. The organic layer was dehydrated with magnesium sulfate, and was filtered. A filtrate thus obtained was concentrated under reduced pressure, and the resultant reaction solution was concentrated under reduced pressure. Thereby, a dry substance in which 4-iodotoluene (referred to as "4-I body" in Table 1) and 2-iodotoluene (referred to as "2-I body" in Table 1) were mixed together was obtained. Table 1 shows a yield of the resultant reaction product and a mixture ratio of the 4-iodotoluene and 2-iodotoluene.

Example 2

In Example 2, production of an iodine cation was carried out in the same manner as Example 1, except that 5.0 mol/L of a methanesulphonic acid solution was used as the supporting electrolyte. As a result, an aromatic iodine compound was obtained. Table 1 shows a yield of the resultant reaction product and a mixture ratio of 4-iodotoluene and 2-iodotoluene.

Example 3

In Example 3, production of an iodine cation was carried out in the same manner as Example 1, except that 4.0 mol/L of a phosphoric acid solution was used as the supporting electrolyte. As a result, an aromatic iodine compound was obtained. Table 1 shows a yield of the resultant reaction product and a mixture ratio of 4-iodotoluene and 2-iodotoluene.

Example 4

In Example 4, production of an iodine cation was carried out in the same manner as Example 1, except that 2.0 mol/L of trifluoromethanesulphonic acid was used as the supporting electrolyte, and electrolysis was carried out at −20° C. As a result, an aromatic iodine compound was obtained. Table 1 shows a yield of the resultant reaction product and a mixture ratio of 4-iodotoluene and 2-iodotoluene.

Example 5

In Example 5, production of an iodine cation was carried out in the same manner as Example 1, except that 2.0 mol/L of benzenesulphonic acid was used as the supporting electrolyte. As a result, an aromatic iodine compound was obtained. Table 1 shows a yield of the resultant reaction product and a mixture ratio of 4-iodotoluene and 2-iodotoluene.

Comparative Example 1

In Comparative Example 1, reaction was carried out in the same manner as Example 1, except that 4.59 mol/L of trifluoroacetic acid was used as the supporting electrolyte. However, a current did not flow even when a voltage up to 110V was applied. For this reason, iodine molecules were not electrolyzed, and an iodine cation solution could not be obtained.

TABLE 1

|  | Supporting Electrolyte | Solvent | Yield (%) | 4-I/2-I |
|---|---|---|---|---|
| Example 1 | $H_2SO_4$ | $CH_3CN$ | 87.2 | 55/45 |
| Example 2 | $MeSO_3H$ | $CH_3CN$ | 67.0 | 56/44 |
| Example 3 | $H_3PO_4$ | $CH_3CN$ | 32.0 | 67/33 |
| Example 4 | $CF_3SO_3H$ | $CH_3CN$ | 61.8 | 70/30 |
| Example 5 | $C_6H_5SO_3H$ | $CH_3CN$ | 42.3 | 62/38 |
| Comparative Example 1 | $CF_3COOH$ | $CH_3CN$ | — |  |

In Examples 1 through 5, it was possible to produce iodotoluene by causing a solution obtained by electrolysis and toluene to react with each other. From the results, it was confirmed that the iodine cation was produced by the electrolysis in Examples 1 through 5.

Example 6

A solution containing an iodine cation was produced in the same manner as Example 1. To 12.5 ml of the iodine cation solution, 10 ml of 1,2-diethoxyethane was added. Then, 92 mg (1.0 mmol) of toluene and 2.5 ml of 1,2-dimethoxyethane were provided in a 50 ml eggplant-shaped flask, agitated with the use of a magnetic stirrer, and cooled down to 0° C. in an ice bath. Into the flask, 22.5 ml of the iodine cation solution was added, and left for one hour at 0° C. The resultant reaction solution was concentrated under reduced pressure, and then dried. Thereby a reaction product was obtained. The reaction product thus obtained was 4-iodotoluene and 2-iodotoluene. A yield of the reaction product was 79.8%, and a mixture ratio of 4-iodotoluene and 2-iodotoluene was 73:27.

From a result of Example 6, it was confirmed that, by using, as a solvent of iodizing reaction, diethoxyethane that is an ether compound, an aromatic iodine compound in which iodine was bound in a para-position was produced with high productivity.

Example 7 Through Example 29

In Examples 7 through 29, an aromatic iodine compound was obtained in the same manner as Example 1, except that an aromatic compound was replaced with a compound shown in Table 2.

TABLE 2

| Example | Aromatic Compound (Substrate) | Yield | Product Ar-1 | Ratio of Isomers |
|---|---|---|---|---|
| 7 | Et–C6H5 | 85.6$^c$ | Et–C6H4–I (para) and Et–C6H4–I (ortho) | 71/29 |
| 8 | i-Pr–C6H5 | 89.7$^c$ | i-Pr–C6H4–I (para) and i-Pr–C6H4–I (ortho) | 86/14 |
| 9 | t-Bu–C6H5 | 91.3$^c$ | t-Bu–C6H4–I (para) and t-Bu–C6H4–I (ortho) | 96/4 |
| 10 | biphenyl | 82.3$^f$ | 4-iodobiphenyl and 2-iodobiphenyl | 96/4 |
| 11 | biphenyl | 79.4$^{c,g}$ | 4,4′-diiodobiphenyl and 2,4′-diiodobiphenyl | 93/7 |
| 12 | naphthalene | 63.7$^e$ | 1-iodonaphthalene | — |
| 13 | HO–C6H5 | 56.0$^b$ | HO–C6H4–I (para) and HO–C6H4–I (ortho) (HO–C6H4–I (meta) 14.0%) | 93/7 |

TABLE 2-continued

| Example | Aromatic Compound (Substrate) | Yield | Product Ar-1 | Ratio of Isomers |
|---|---|---|---|---|
| 14 | MeO–C₆H₅ | 72.4[b] | MeO-C₆H₄-I (p), MeO-C₆H₄-I (o), (MeO-C₆H₃-I₂ 5.9%) | 93/7 |
| 15 | thiophene | 16.3[b] | 2-iodothiophene, (2,5-diiodothiophene 28.1%) | — |
| 16 | 2-acetylthiophene | 51.7[b] | 5-iodo-2-acetylthiophene, (diiodo-acetylthiophene ?) | — |
| 17 | H₂N–C₆H₅ | 9.7[b] | H₂N-C₆H₄-I (p), H₂N-C₆H₄-I (o) | 92/8 |
| 18 | Cl–C₆H₅ | 28.6[f] | Cl-C₆H₄-I (p), Cl-C₆H₄-I (o) | 83/17 |
| 19 | Br–C₆H₅ | 12.4[e] | Br-C₆H₄-I (p), Br-C₆H₄-I (o) | 79/21 |
| 20 | I–C₆H₅ | 21.0[f] | I-C₆H₄-I (p), I-C₆H₄-I (o) | 72/28 |
| 21 | NC–C₆H₅ | 22.1[b] | NC-C₆H₄-I (m) | — |
| 22 | p-xylene | 69.2[a] | iodo-p-xylene, (diiodo-p-xylene 6.3%) | — |
| 23 | o-xylene | 86.9[e] | 4-iodo-o-xylene, 3-iodo-o-xylene | 83/17 |

TABLE 2-continued

| Example | Aromatic Compound (Substrate) | Yield | Product Ar-1 | Ratio of Isomers |
|---|---|---|---|---|
| 24 | 1,3-dimethylbenzene | 86.3$^e$ | 2,4-dimethyl-1-iodobenzene / 2,6-dimethyl-1-iodobenzene | 93/7 |
| 25 | 4-chlorotoluene | 27.3$^e$ | 3-iodo-4-chlorotoluene / 2-iodo-4-chlorotoluene | 68/32 |
| 26 | 2-chlorotoluene | 45.7$^e$ | four isomers of iodo-2-chlorotoluene | 60/8/26/7 |
| 27 | 4-chlorophenol | 62.0$^e$ | 2-iodo-4-chlorophenol | — |
| 28 | 4-methoxytoluene | 92.0$^e$ | 2-iodo-4-methoxytoluene | — |
| 29 | 2-methoxytoluene | 91.4$^e$ | 4-iodo-2-methoxytoluene | — |

$^a$based on I$_2$.
$^b$GC Yield.
$^c$isolated yield.
$^d$mixture of regioisomer.
$^e$determined by $^1$H-NMR analysis.
$^f$2.2 eq. of "I$^+$" was used.
$^g$based on substrate.

As shown in Table 2, it was confirmed that, according to present examples, it is possible to successfully obtain an aromatic iodine compound with the use of the iodine cation.

Example 30 Through Example 42

(Production of Iodine Cation)

With the use of the same device as in Example 1, 56 ml of an acetonitrile solution containing 2.0M of sulfuric acid was provided in a cathode room, and 56 ml of an acetonitrile solution containing 2.0M of sulfuric acid, and 1.524 g (6 mmol) of iodine molecules were provided in an anode room. Then, the device was cooled down to 0° C. While the cathode room and the anode room were agitated with the use of a magnetic stirrer, a 20 mA current was caused to flow in the device at 0° C. so as to carry out electrolysis. By applying 2.0 F/mol of electricity, an iodine cation solution was obtained from the anode room. The iodine cation solution thus obtained was put in an eggplant-shaped flask, and left in a constant-temperature bath at −20° C.

(Production of Aromatic Iodine Compound)

After the iodine cation solution was obtained in the method described above, 2 ml (approximately 0.12M, 0.42 mmol) of the iodine cation solution was taken by use of a syringe, and a solvent shown in Table 3 was added to the iodine cation solution thus taken. Then the iodine cation solution was added, via a cannula, into a flask in which 77.4 mg (0.84 mmol) of toluene was provided in advance. Reaction took place for 30 minutes at 0° C. After the reaction was completed, the solution was neutralized with an aqueous sodium hydroxide. Then, ether was added to the solution, so that an aqueous layer was extracted. After being washed with a supersaturated salt solution once, an ether layer was dried with magnesium sulfate, and filtered. A filtrate thus obtained was subjected to gas chromatograph analysis (internal reference method). The following Table 3 shows a yield of the resultant product (4-iodotoluene and 2-iodotoluene) and a mixture ratio of 4-iodotoluene and 2-iodotoluene.

TABLE 3

|  | Solvent | Amount of solvent (ml) | Yield Constant (%) | Ratio (4-I/2-I) |
|---|---|---|---|---|
| Example 30 | Propionitrile | 2.0 | 90.9 | 57/43 |
| Example 31 | Isobutyronitrile | 2.0 | 68.4 | 56/44 |
| Example 32 | 1,1,1-trimethoxyethane | 2.0 | 22.9 | 76/24 |
| Example 33 | 1,1,1-trimethoxy-2-methylpropane | 0.3 | 79.7 | 62/38 |
| Example 34 | Diethyl ether | 2.0 | 88.7 | 64/36 |
| Example 35 | Diisopropyl ether | 2.0 | 15.0 | 59/41 |
| Example 36 | Methanol | 1.0 | 32.0 | 68/32 |
| Example 37 | Ethanol | 2.0 | 10.9 | 67/33 |
| Example 38 | Propanol | 2.0 | 23.3 | 63/37 |
| Example 39 | Butanol | 2.0 | 38.1 | 63/37 |
| Example 40 | Pentafluoro acetic acid | 0.7 | 84.1 | 54/46 |
| Example 41 | 70% Phosphoric acid aqueous solution | 1.0 | 37.1 | 63/37 |
| Example 42 | Dichloromethane | 2.0 | 50.9 | 55/45 |

From results of Examples 30 through 42, it was confirmed that, even in a case where various solvents are used, an aromatic compound can be iodized.

Production of Aromatic Iodine Compound

Example 43

(Production of Iodine Cation)
Production of an iodine cation was carried out with the use of an H-type 2-room electrolytic cell under an anhydrous condition. At that time, a glass filter (G4) was used as a diaphragm. As an anode electrode and a cathode electrode, platinum plates (30 mm×20 mm) were used. The electrolytic cell was dried under reduced pressure, and was filled with nitrogen atmosphere. Then, 8 mL of an acetonitrile solution in which 79 mg (0.526 mmol) of trifluoromethanesulphonic acid and 0.3M of tetrabutylammoniumtetrafluoroborate (supporting electrolyte) were dissolved was provided in a cathode room, and 8 mL of an acetonitrile solution in which 0.3M tetrabutylammoniumtetrafluoroborate (supporting electrolyte) was dissolved and 127 mg (0.500 mmol) of iodine were provided in an anode room. After that, the electrolytic cell was cooled down to 0° C. While the anode room and the cathode room were agitated with the use of a magnetic stirrer, electrolysis was carried out with a constant current (20 mA) at 0° C. By applying 2.0 F/mol of electricity, an iodine cation solution was obtained from the anode room.

(Production of Aromatic Iodine Compound)
Next, 92 mg (1.0 mmol) of toluene which is an aromatic compound having one substituent group and 8 ml of 1,2-dimethoxyethane which is an acyclic ether compound were provided in a 50 ml eggplant-shaped flask, agitated with the use of a magnetic stirrer, and cooled down to 0° C. in an ice bath. Into the flask, 12.5 ml of the iodine cation solution obtained by the electrolysis was added, and reaction took place for one hour at 0° C. The resultant reaction solution thus obtained was concentrated under reduced pressure, and was put in a 10 cm silica gel column, so as to cause a resultant reaction product to be dissolved out from the column with the use of 100 ml of ether. A solvent was concentrated under reduced pressure, and 100 ml of a saturated sodium hydrogen carbonate solution and 50 ml of hexane were added to the reaction product. Thereby, extraction was carried out. After liquid separation process was carried out, a hexane layer was concentrated under reduced pressure, and the reaction product was dried. The reaction product thus obtained was a mixture of 4-iodotoluene and 2-iodotoluene. The following Table 4 shows a yield and a ratio of the reaction product. It should be noted that in Table 4, a product in which iodine is bound in a para-position is referred to as "I", and a product in which iodine is bound in an ortho position is referred to as "II". Further, the ratio was determined from a measurement result of $^1$H-NMR.

(Recrystallization)
The reaction product thus obtained was dissolved in 0.7 ml of methanol, and a crystal was separated out at −40° C. This operation was carried out twice, so that a reaction product in which a degree of purity of 4-iodotoluene was 98% was obtained.

Example 44 Through Example 48

(Production of Iodine Cation)
In a cathode room of an electrolytic cell, 8 mL of an acetonitrile solution containing 2.0M of sulfuric acid was provided, and in an anode room of the electrolytic cell, 8 mL of an acetonitrile solution containing 2.0M of sulfuric acid, and 127 mg (0.50 mmol) of iodine molecules were provided. While the anode room and the cathode room were agitated with the use of a magnetic stirrer, electrolysis was carried out with a constant current (20 mA) at 25° C. Then 2.0 F/mol of electricity was applied. As a result, an iodine cation solution was obtained.

(Production of Aromatic Iodine Compound)
Next, 92 mg (1.0 mmol) of toluene was dissolved in 3.6 mL of 1,2-dimethoxyethane, and the resultant solution was cooled down to a temperature shown in Table 4. Then, the iodine cation solution thus obtained was added to the solution, and reaction took place for one hour at the temperature of the above cooling process. After the reaction was completed, an aqueous sodium hydroxide and ether were added to the solution, so as to neutralize the solution. The solution was separated into an ether layer and an aqueous layer. The ether layer and the aqueous layer were liquid-separated. Then ether was added to the aqueous layer, so as to liquid-separated the aqueous layer. This operation was carried out twice. The ether layers thus obtained was mixed together, and was washed with a saturated saline. The resultant product was concentrated under reduced pressure. Thereby a dried product was obtained. The resultant product thus obtained was 4-iodotoluene and 2-iodotoluene. The following Table 4 shows a yield and a ratio of the product.

TABLE 4

|  | Ether compound | Reaction temperature | Yield (%) | Ratio (I/II) |
|---|---|---|---|---|
| Example 43 | DME | 0° C. | 42.4 | 79/21 |
| Example 44 | DME | 25° C. | 52.1 | 70/30 |
| Example 45 | DME | 0° C. | 73.2 | 72/28 |
| Example 46 | DME | −20° C. | 75.4 | 74/26 |
| Example 47 | DME | −30° C. | 75.1 | 75/25 |
| Example 48 | DME | −40° C. | 75.7 | 77/23 |

Abbreviation: DME stands for 1,2-dimethoxyethane.

Example 49 Through Example 52

In Examples 49 through 52, 4-iodotoluene and 2-iodotoluene were obtained in the same manner as Example 43, except that an ether compound was replaced with a compound shown in the following Table 5. The following Table 5 shows a yield and a ratio of a resultant product.

TABLE 5

| | Ether compound | Reaction temperature | Yield (%) | Ratio (I/II) |
|---|---|---|---|---|
| Example 49 | 1,4 dioxane | 0° C. | 52.4 | 75/25 |
| Example 50 | Tetrahydrofuran | 0° C. | 33.0 | 75/25 |
| Example 51 | Diethyleneglicoldimethyl ether | 0° C. | 18.0 | 82/18 |
| Example 52 | Tetraethyleneglicoldimethyl ether | 0° C. | 10.4 | 75/25 |

Example 53

(Production of Iodine Cation)

An iodine cation solution was obtained in the same manner as Example 43, except that 13 mL of an acetonitrile solution containing 2.0M of sulfuric acid (supporting electrolyte) was provided in a cathode room of an electrolytic cell, and 13 mL of an acetonitrile solution containing 2.0M of sulfuric acid, and 127 mg (0.500 mmol) of iodine were provided in an anode room of the electrolytic cell.

(Production of Aromatic Iodine Compound)

Next, 12.5 ml (1.0 mmol) of the iodine cation solution thus obtained was added to 10 ml of dimethoxyethane (an acyclic ether compound). The resultant solution was added to a mixture of 92 mg (1.0 mmol) of toluene and 2.5 ml of dimethoxyethane, which is an acyclic ether compound. Then reaction took place. At this point, a temperature of the reaction was 0° C. The solution was agitated for a half hour. After the reaction was completed, 13 mL of a 4N aqueous sodium hydroxide was added to the solution at 0° C., so as to neutralize the solution. Then 20 mL of ether was added to the solution so as to dilute the solution. A reaction mixture thus obtained was put in a separatory funnel, so that the reaction mixture was separated into an organic layer and an aqueous layer. The aqueous layer was extracted with ether, and the organic layer was washed with a saturated saline. The organic layer was dried with the use of magnesium sulfate, and then was filtered. A filtrate thus obtained was concentrated under reduced pressure, and the resultant reaction solution was concentrated under reduced pressure. As a result, a dried product in which 4-iodotoluene and 2-iodotoluene were mixed together was obtained. Table 6 shows a yield of the resultant reaction product of Example 53 and a production ratio of 4-iodotoluene and 2-iodotoluene.

Example 54 Through Example 61

In Examples 54 through 61, an aromatic iodine compound was obtained in the same manner as Example 53, except that an aromatic compound (a starting compound) was replaced with a compound shown in Table 6. The following Table 6 shows a yield and a ratio of a resultant product.

Comparative Example 2

In Comparative Example 2, production of an iodine cation was carried out in the same manner as Example 53. Then, an iodine cation solution thus obtained was added to 12.5 ml of an acetonitrile solution containing toluene. After that, the resultant solution was agitated for one hour. The resultant reaction solution was concentrated under reduced pressure, and thereby a reaction product containing 4-iodotoluene and 2-iodotoluene was obtained. The following Table 6 shows a yield and a ratio of the resultant product.

Comparative Example 3 Through Comparative Example 10

In Comparative Examples 3 through 10, an aromatic iodine compound was obtained in the same manner as Comparative Example 2, except that an aromatic compound (starting compound) was replaced with another compound. The following Table 6 shows a yield of the aromatic iodine compound and a ratio of a binding position of iodine in the aromatic iodine compound. It should be noted that in Table 6, Comparative Examples 2 through 10 correspond to Examples 53 through 61 respectively. Results of Comparative Examples are associated with the results of the corresponding Examples in Table 6.

TABLE 6

| | Aromatic Compound (Substrate) | Product Yield (%)[a,d] | Product | | Ratio of isomers |
|---|---|---|---|---|---|
| Example 53 Comparative example 2 |  | 79.8[c] 87.9[c] | 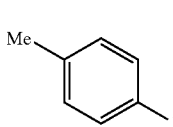 | 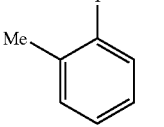 | 73/27 57/43 |
| Example 54 Comparative example 3 | 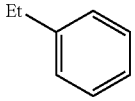 | 82.1[c] 85.6[c] | 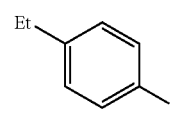 | 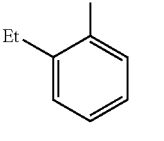 | 82/18 71/29 |
| Example 55 Comparative example 4 | 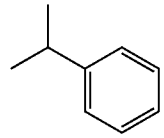 | 84.8[c] 89.7[c] | 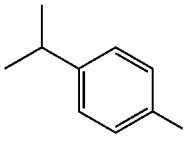 | 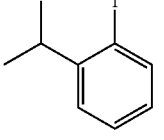 | 91/9 86/14 |

TABLE 6-continued

| | Aromatic Compound (Substrate) | Yield (%)[a,d] | Product | Ratio of isomers |
|---|---|---|---|---|
| Example 56 Comparative example 5 | 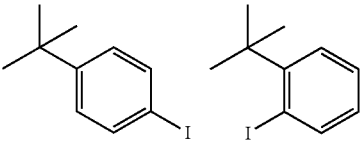 | 89.3[c] 91.3[c] | 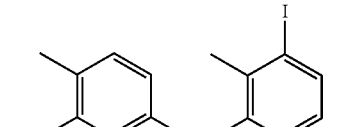 | 97/3 96/4 |
| Example 57 Comparative example 6 | 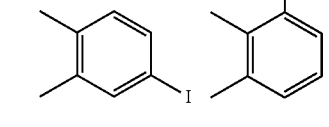 | 81.0[e] 86.9[c] | 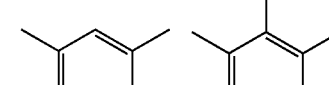 | 88/12 83/17 |
| Example 58 Comparative example 7 | 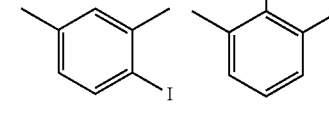 | 82.4[e] 86.3[c] | 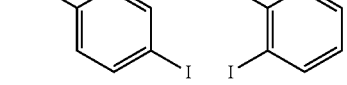 | 94/6 93/7 |
| Example 59 Comparative example 8 | 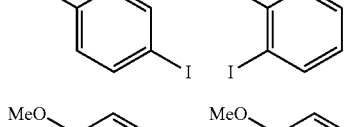 | 88.8[b] 56.0[b] | 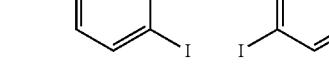 | 98/2 93/7 |
| Example 60 Comparative example 9 | 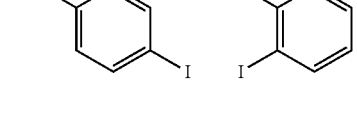 | 82.3[b] 72.4[b] | 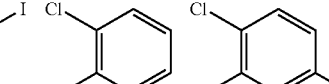 | 97/3 93/7 |
| Example 61 Comparative example 10 | 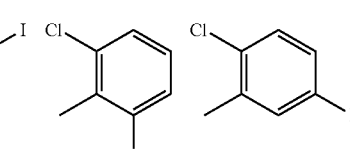 | 12.5[c] 45.7[e] | 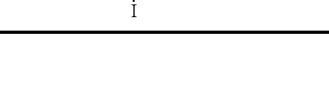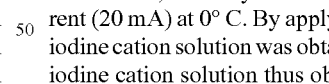 | 64/7/23/7 60/8/26/7 |

[a]based on $I_2$.
[b]GC Yield.
[c]isolated yield.
[d]mixture of regioisomer.
[e]determined by $^1$H-NMR analysis.

As clearly seen from Tables 4 through 6, it was confirmed that according to the method of Examples, for producing an aromatic iodine compound, an aromatic iodine compound in which iodine was bound in a para-position was produced with high selectivity. Further, as seen from comparisons between Examples 43 through 48, it was confirmed that the selectivity is improved as a reaction temperature in iodization becomes low.

Example 62 Through Example 73

(Production of Iodine Cation)

In a cathode room of an electrolytic cell, 56 ml of an acetonitrile solution containing 2.0M of sulfuric acid was provided, and in an anode room of the electrolytic cell, 56 ml of an acetonitrile solution containing 2.0M of sulfuric acid, and 1.524 g (6 mmol) of iodine molecules were provided. Then the electrolytic cell was cooled down to 0° C. While the cathode room and the anode room were agitated by a magnetic stirrer, electrolysis was carried out with a constant current (20 mA) at 0° C. By applying 2.0 F/mol of electricity, an iodine cation solution was obtained from the anode room. The iodine cation solution thus obtained was put in an eggplant-shaped flask, and then was left in a constant-temperature bath at −20° C.

(Production of Aromatic Iodine Compound)

After the iodine cation solution was obtained by the method described above, 2 ml (approximately 0.21M, 0.42 mmol) of the iodine cation solution was taken with the use of a syringe. Then an ether compound (solvent) shown in Table 7 was added to the iodine cation solution thus taken. After that, the resultant solution was added, via a cannula, into a flask in which 77.4 mg (0.84 mmol) of toluene was provided in advance. Then reaction took place for a half hour at 0° C. After the reaction was completed, the resultant solution was neutralized with the use of an aqueous sodium hydroxide. Then ether was added to the resultant solution, so as to extract an aqueous layer. An ether layer was washed with a saturated saline once, dried with the use of magnesium sulfate, and filtered. A filtrate thus obtained was subjected to gas chromatograph analysis (internal reference method). Table 7 shows a yield of the resultant product, and a production ratio of 4-iodotoluene and 2-iodotoluene.

TABLE 7

| | Ether compound | Yield (%)[a,b] | Ratio (I/II) |
|---|---|---|---|
| Example 62 | DME (2.0 ml) | 92.0 | 71/29 |
| Example 63 | DEE (2.0 ml) | 91.8 | 66/34 |
| Example 64 | TEGDE (2.0 ml) | 85.3 | 67/33 |
| Example 65 | 1,4-dioxane (1.0 ml) | 90.2 | 66/34 |
| Example 66 | Diethyleneglicoldimethyl ether (5.0 ml) | 47.5 | 72/22 |
| Example 67 | Ethyleneglicol (2.0 ml) | 49.3 | 66/34 |
| Example 68 | PEG400 (2.0 ml) | 65.0 | 61/39 |
| Example 69 | Et$_2$O (2.0 ml) | 88.7 | 64/36 |
| Example 70 | i-Pr$_2$O (2.0 ml) | 15.7 | 59/41 |
| Example 71 | THF (2.0 ml) | 68.4 | 68/32 |
| Example 72 | Tetrahydropyran (2.0 ml) | 72.3 | 69/31 |
| Example 73 | Trimethoxyethane (2.0 ml) | 22.9 | 76/24 |

[a]based on I$_2$.
[b]GC Yield.
c: 5.0 mL (0.670 mmol) of iodine cation solution.
DEE: 1,2-diethoxyethane.
TEGDE: tetraethyleneglicoldimethyl ether.

As seen from results shown in Table 7, it was confirmed that even in a case where various ether compounds are used, an aromatic iodine compound can be produced successfully.

With the method of the present invention, for producing an iodizing agent, an iodine cation can be produced by electrolyzing iodine molecules by using an acid as a supporting electrolyte. In a case where an iodine compound is obtained by use of an iodine cation solution thus obtained, it is unnecessary to carry out a sophisticated separation operation using column chromatography after reaction is completed. Therefore, it is possible to produce an iodine cation which is suitably used as an iodizing agent suitable for industrial production of an iodine compound.

Further, according to a method of present invention, for producing an aromatic iodine compound, as described above, it is possible to increase selectivity of a binding position of an iodine atom with respect to an aromatic compound by causing an iodizing agent and an aromatic compound having one or more substituent groups to react with each other under the presence of a certain ether compound.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

A method of the present invention, for producing an iodizing agent, can be applied to iodization of various compounds, and can be used to produce an iodine cation which is suitable for industrial production. Further, with a method of the present invention, for producing an aromatic iodine compound, it is possible to produce an aromatic iodine compound which is suitably used as a reaction intermediate.

The invention claimed is:

1. A method of producing an aromatic iodine compound, comprising the step of (a) causing an iodizing agent, and an aromatic compound whose nucleus has one or more substituent groups and two or more hydrogen atoms, to react with each other under the presence of at least one selected from the group consisting of cyclic or acyclic ether compounds, wherein the acyclic ether compound is represented by the following General Formula (3):

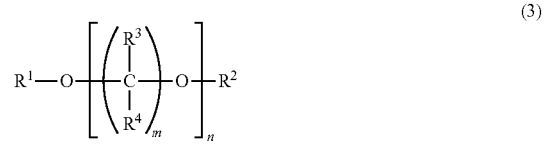

where: m is any integer in a range from 2 to 6; n is an integer not less than 1; $R^1$ and $R^2$ are identically or differently a hydrogen atom or a $C_{1-10}$ alkyl group; $R^3$ and $R^4$ are identically or differently a hydrogen atom or a $C_{1-10}$ alkyl group.

2. The method of producing an aromatic iodine compound, according to claim 1, wherein:
the cyclic ether compound contains a $C_{3-12}$ ring.

3. The method of producing an aromatic iodine compound, according to claim 1, wherein:
the iodizing agent is an iodine cation.

4. The method of producing an aromatic iodine compound, according to claim 1, further comprising the steps of:
separating a solid reaction product from a reaction solution obtained in the step (a); and
recrystallizing the reaction product thus separated from the reaction solution.

5. The method of producing an aromatic iodine compound, according to claim 1, further comprising the step of isolating a reaction product by carrying out distillation process with respect to a reaction solution obtained in the step (a).

* * * * *